United States Patent [19]

Tsuchiya et al.

[11] Patent Number: 5,047,353

[45] Date of Patent: Sep. 10, 1991

[54] PROCESS FOR PREPARING REAGENT FOR MEASURING ENDOTOXIN

[75] Inventors: Masakazu Tsuchiya, Itami; Shuji Matuura, Kawanishi, both of Japan

[73] Assignee: Wako Pure Chemical Industries, Ltd., Osaka, Japan

[21] Appl. No.: 323,719

[22] Filed: Mar. 15, 1989

[30] Foreign Application Priority Data

Mar. 16, 1988 [JP] Japan .................................. 63-62142

[51] Int. Cl.$^5$ .......................................... G01N 33/579
[52] U.S. Cl. ...................... 436/502; 435/4; 435/23; 436/501
[58] Field of Search ....................... 435/23, 13, 4, 69.1; 436/502, 501; 210/656; 422/73; 530/417, 810, 820

[56] References Cited

U.S. PATENT DOCUMENTS 4,038,029  7/1977  Teller et al. ............................ 23/230
4,606,824  8/1986  Chu et al. ............................. 210/656

FOREIGN PATENT DOCUMENTS 0056210  12/1981  European Pat. Off. .
58-13516  1/1983  Japan .
59-27828  2/1984  Japan .

OTHER PUBLICATIONS

Obayashi et al., A New Chromogenic Endotoxin-Specific Assay Using Recombined Limulus Coagulation Enzymes..., Clinica Chimica Acta, 149 (1985) 55–65.
Kakinuma et al., *Biochemical and Biophysical Research Communications*, 101, 434–439, (1981).
Homma et al., *Bacterial Endotoxin*, 365–382, (1984).
Obayashi et al., Clinica Chemica Acta, 149, 55–65, (1985).
Patent Abstracts of Japan, vol. 8, No. 114, May 26, 1984.
Chemical Abstracts, vol. 95, No. 15, Oct. 12, 1989, p. 27.
International Publication No. WO 83/02123, published Jun. 23, 1983.

*Primary Examiner*—Sam Rosen
*Attorney, Agent, or Firm*—Armstrong, Nikaido, Marmelstein, Kubovcik & Murray

[57] ABSTRACT

A reagent obtained by bringing an extracted solution of horseshoe crab hemocyte lysate into temporary contact with a treating agent such as a water-insoluble polysaccharide containing $\beta$-1,3-glucosidic linkage and freeing the extracted solution from said treating agent is effective for specifically measuring endotoxin.

8 Claims, 2 Drawing Sheets

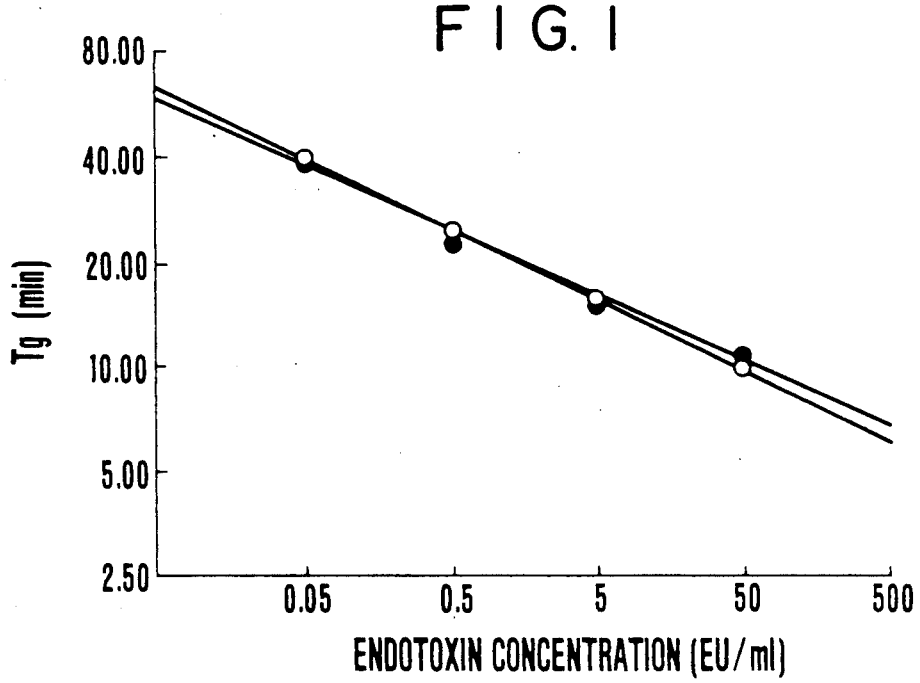
FIG. I
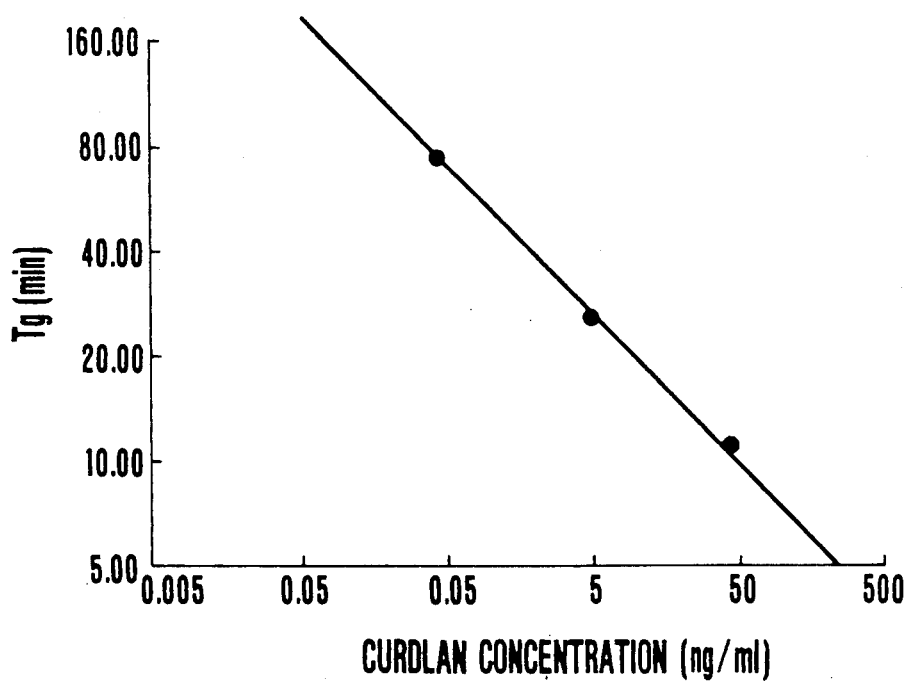
FIG. 2

PROCESS FOR PREPARING REAGENT FOR MEASURING ENDOTOXIN

BACKGROUND OF THE INVENTION

This invention relates to a process for preparing a reagent for measuring endotoxin by using an extracted solution of hemocyte lysate (amoebocyte lysate) of horseshoe crab (hereinafter abbreviated as "AL solution") as a starting material, the reagent thus prepared and processes for measuring endotoxin using said reagent.

Endotoxins (hereinafter abbreviated as "ET's") are lipopolysaccharides present mainly in cell wall of Gram-negative bacteria and are known as pyrogens. Therefore, the measurement of ET concentration in a sample is one important measurement in the fields of medical science, pharmacy and microbiology.

At present, as a method for measuring ET, the so-called Limulus test utilizing the phenomenon that AL solution is activated by ET to form gel clot is widely employed because of its simplicity, convenience, low cost, etc.

However, it was found that AL solution reacts not only with ET's but also with carboxymethylated $\beta$-1,3-glucan [Kakinuma et al., Biochem. Biophys. Research Communication, 101(2), 434–439 (1981)]. It was proved that this phenomenon is caused by the reaction of a factor (hereinafter abbreviated as "GL-sensitive factor") present in AL solution which reacts with $\beta$-1,3-glucan (hereinafter abbreviated as "GL") to trigger coagulation with GL or a derivative thereof (Bacterial Endotoxin, published by Verlay Chemic, 365–382, 1984).

Therefore, most of commercially available Limulus test reagents react not only with ET but also with GL, so that it is difficult to judge which of ET, GL and a mixture thereof is present in a sample, by the Limulus test. Thus, the specificity of such Limulus test reagents is a problem.

In order to solve this problem, there has been reported a method for preparing a reagent specific for ET by removing GL-sensitive factor from AL solution [Japanese Patent Appln. Kokai (Laid-Open) Nos. 58-13516 and 59-27828]. However, all the methods disclosed in these references require a very troublesome procedure of treating AL solution, for example, by a gel filtration method or a chromatographic method using a carrier having heparin or dextran sulfate attached thereto, to separate the AL solution into a fraction of proclatting enzyme, a fraction of GL-sensitive factor, and a fraction of a factor (hereinafter abbreviated as "ET-sensitive factor") which reacts with ET to trigger coagulation in order to remove the GL-sensitive factor. Therefore, for preventing AL solution or the fractions obtained therefrom from being contaminated by ET during the separation procedures, there are required, for example, facilities used exclusively for carrying out said procedures. Moreover, the above methods are further disadvantageous in that the individual fractions should be properly mixed again in order to obtain a reagent specific for ET.

SUMMARY OF THE INVENTION

This invention was made in consideration of such conditions, and is intended to provide a simple and efficient removing process of GL-sensitive factor for obtaining a reagent specific for ET by using AL solution as a starting material.

This invention provides a process for preparing a reagent for measuring endotoxin which comprises bringing an extracted solution of horseshoe crab hemocyte lysate into temporary contact with at least one treating agent selected from the group consisting of (a) a water-insoluble polysaccharide containing $\beta$-1,3-glucosidic linkage, (b) a water-insoluble polysaccharide derivative containing $\beta$-1,3-glucosidic linkage, (c) a polysaccharide containing $\beta$-1,3-glucosidic linkage and being fixed on a water-insoluble carrier, and (d) a polysaccharide derivative containing $\beta$-1,3-glucosidic linkage and being fixed on a water-insoluble carrier, and freeing the extracted solution of horseshoe crab hemocyte lysate from said treating agents (a) to (d).

This invention also provides a reagent for measuring endotoxin thus prepared.

This invention further provides processes for measuring endotoxin using the reagent thus prepared.

BRIEF DESCRIPTION OF THE DRAWINGS

FIG. 1 shows calibration curves for endotoxin which were obtained in Referential Example 1 and Comparative Example 1.

FIG. 2 shows a calibration curve for curdlan which was obtained in Comparative Example 1.

DESCRIPTION OF THE PREFERRED EMBODIMENTS

Figure 3:
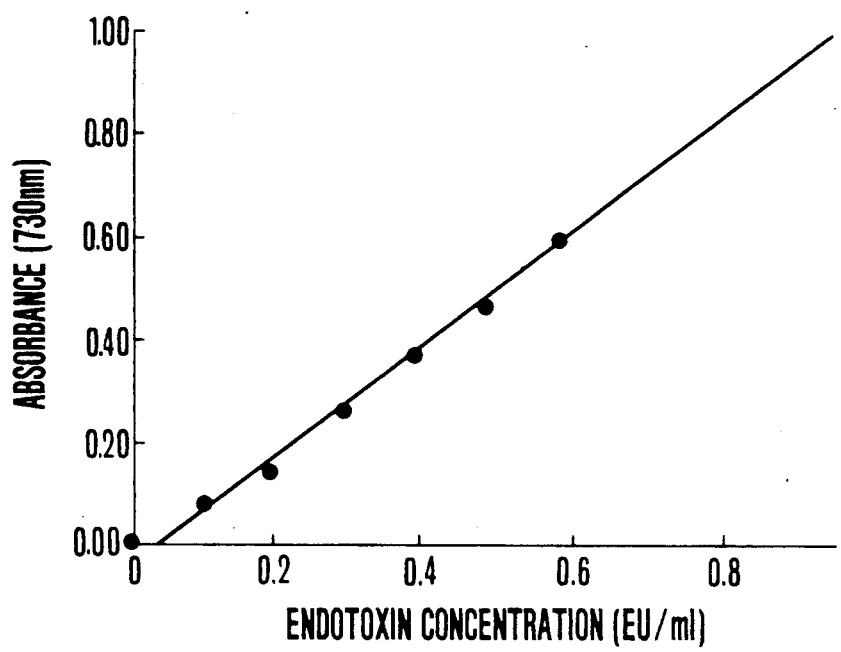
FIG. 3 shows a calibration curve for endotoxin which was obtained in Referential Example 3.

In the present specification, the following abbreviations are used:

ET: endotoxin

AL solution: an extracted solution of hemocyte lysate of horseshoe crab

GL: $\beta$-1,3-glucan

GL-sensitive factor: a factor present in AL solution which reacts with GL

ET-sensitive factor: a factor which reacts with ET to trigger coagulation

GLNSPS: a water-insoluble polysaccharide containing $\beta$-1,3-glucosidic linkage GLPS: a polysaccharide containing $\beta$-1,3-glucosidic linkage LAL: a freeze-dried product of AL solution derived from horseshoe crab belonging to Limulus genus CT-LAL solution: a reagent specific for ET obtained in Example 1

ZT-LAL solution: a reagent specific for ET obtained in Example 2

Tg: a time required for reducing the transmittance by 5% untreated LAL solution: a LAL solution prepared by dissolving LAL of the same lot as in Example 1 in 5 ml of distilled water for injection.

The present inventors earnestly investigated a process for easy and efficient preparation of a reagent specific for ET (i.e. useful for measuring ET) by use of AL solution as a starting material, and consequently found that a reagent which reacts specifically with ET can easily be obtained by bringing AL solution into contact with the following at least one polysaccharide comprising glucose residues linked in the manner of GL which is known to coagulate AL solution: either (a) a water-insoluble polysaccharide containing β-1,3-glucosidic linkage (hereinafter abbreviated as "GLNSPS") and/or (b) a water-insoluble derivative of a polysaccharide containing β-1,3-glucosidic linkage (hereinafter a polysaccharide containing β-1,3-glucosidic linkage is abbreviated as "GLPS"), or [(c) and (d)] GLPS and/or derivative thereof fixed on an insoluble carrier, for example, by addition of a large amount of the GLNSPS and/or the water-insoluble derivative of GLPS, or the GLPS and/or derivative thereof fixed on a water-insoluble carrier to the AL solution, and then freeing therefrom the AL solution. Thus, this invention has been accomplished.

As the GLNSPS and GLPS which are usable in this invention, any GLPS or derivative thereof which is insoluble in AL solution can be used without particular limitation. More specifically, preferable examples of GLNSPS include water-insoluble polysaccharides selected from polysaccharides generally known as GLPS, for example, natural polysaccharides obtained from various bacteria (e.g. Alcaligenes genus, Agrobacterium genus, etc.), yeasts (e.g. Saccharomyces genus, etc.), and mushrooms (e.g. a shiitake (*Cortinellus shiitake*), *Schizophyrum commune, Coriolus verisicolor*, etc.), specific examples of the natural polysaccharides including curdlan, pachyman, sclerotan, lentinan, schizophyllan, coriolan, etc.; storage polysaccharides of algae, e.g. brown algae, Euglena, diatoms, etc., specific examples of the storage polysaccharides including laminaran, paramilon, etc.; and preferable examples of the water-insoluble derivative of GLPS include water-insoluble derivatives obtained by making these natural or storage polysaccharides insoluble in water by a treatment such as heating, and water-insoluble derivatives obtained by introducing at least one group selected from an ethyl group, a butyl group, etc. into the natural or storage polysaccharides according to a conventional method such as the method described, for example, in Munio Kotake "Daiyukikagaku" Vol. 19, 7th ed. Asakura Shoten, May 10, 1967, pp. 70–101. These water-insoluble polysaccharides and water-insoluble derivatives thereof may be used singly or in combination of two or more of them.

In this invention, needless to say, the above-mentioned GLPS's and derivatives thereof which are fixed on a suitable insoluble carrier can be utilized like the GLNSPS and the water-insoluble derivative of GLPS. As the insoluble carrier used for immobilizing the GLPS or derivative thereof, there can be used any of insoluble carriers which are usually used in affinity chromatography, such as cellulose, agarose, dextran, polyacrylamides, porous glass, etc. Among them, agarose is particularly preferable. Specific examples of commercially available insoluble carrier usable in this invention include agarose type carriers such as Sepharose (a trade name, mfd. by Pharmacia Fine Chemicals) and Biogel A (a trade name, mfd. by Bio-Rad Laboratories); dextran type carriers such as Sephadex (a trade name, mfd. by Pharmacia Fine Chemicals) and Sephacryl (a trade name, mfd. by Pharmacia Fine Chemicals); and polyacrylamide type carriers such as Enzafix P (mfd. by Wako Pure Chemical Industries, Ltd.) and Biogel P (a trade name, mfd. by Bio-Rad Laboratories). The insoluble carrier is not limited to these commercially available carriers. For bonding GLPS or a derivative thereof to these insoluble carriers, it is, of course, necessary to activate the insoluble carrier. Although a method for activating the insoluble carrier includes various methods and is not critical, there can be exemplified, for example, a method comprising activation by use of epichlorohydrin, as a suitable method.

As the AL solution usable in this invention, any one can be exemplified without particular limitation so long as it is extracted from hemocytes of horseshoe crab belonging to Limulus genus, Tachypheus genus or Carcinoscorpius genus and reacts with ET to undergo coagulation reaction. It is, of course, possible to use AL solution prepared from freeze-dried products of AL solutions which are commercially available, for example, from Associates of Cape Cod Inc. (ACC), HAEMACHEM, Inc., Whittaker Bioproducts, Inc., etc.

As a method for obtaining a reagent specific for ET by the preparation process of this invention, there can be exemplified without particular limitation any method in which after AL solution is brought into contact either with (a) GLNSPS and/or (b) a water-insoluble derivative of GLPS, and/or with (C) GLPS fixed on a mater-insoluble carrier and/or (d) derivative of GLPS fixed on a water-insoluble carrier, the above-mentioned (a) to (d), i.e. the GLNSPS and/or the water-insoluble derivative of GLPS, and/or the GLPS and/or derivative thereof fixed on water-insoluble carrier can be removed from the AL solution. For example, there can be exemplified a method which comprises adding either (a) GLNSPS and/or (b) a water-insoluble derivative of GLPS, and/or (c) GLPS fixed on a water-insoluble carrier and/or (d) derivative of GLPS fixed on water-insoluble carrier to AL solution to bring the same into contact with the AL solution, and then removing the above-mentioned (a) to (d), i.e., the GLNSPS and/or the water-insoluble derivative of GLPS, and/or the GLPS and/or derivative thereof fixed on an insoluble carrier, by filtration, centrifugation, etc.; and a method which comprises treating AL solution with a column packed with either (a) GLNSPS and/or (b) a water-insoluble derivative of GLPS, and/or (c) GLPS fixed on a water-insoluble carrier and/or (d) derivative of GLPS fixed on water-insoluble carrier.

In the preparation process of this invention, the amount of either the GLNSPS and/or the water-insoluble derivative of GLPS, and/or the GLPS and/or derivative thereof fixed on a water-insoluble carrier which is brought into contact with AL solution is usually such that the amount of GL and/or derivative thereof contained in the GLNSPS and/or the water-insoluble derivative of GLPS, and/or the GLPS and/or derivative thereof fixed on an insoluble carrier which is added to the AL solution is 0.1 W/V % or more based on the AL solution. As the pH at the time of bringing AL solution into contact either with GLNSPS and/or a water-insoluble derivative of GLPS, and/or with GLPS and/or derivative thereof fixed on an insoluble carrier, any pH may be employed so long as it does not inactivate the ET-sensitive factor in the AL solution and factors which participate in coagulation reaction caused by the reaction of ET with the ET-sensitive factor, though a pH in the range of 6 to 8 is usually preferably employed. As the temperature at the time of making the contact, any temperature may be employed so long as it does not inactivate the ET-sensitive factor in the AL solution and the factors which participate in the coagulation reaction caused by the reaction of ET with the ET-sensitive factor, though a temperature of 0° to 40° C., preferably 0° to 10° C. is usually employed.

The form of GLNSPS, a water-insoluble derivative of GLPS, or GLPS and/or derivative thereof fixed on an insoluble carrier which is added to AL solution or packed into a column for treating AL solution is not critical. For example, GLNSPS, a water-insoluble derivative of GLPS, or GLPS and/or derivative thereof fixed on a water-insoluble carrier may be used either as such or after being processed into a suitable form, for instance, after being processed into beads in the case of using curdlan as GLPS, by the process disclosed in Japanese Patent Appln Kokai (Laid-Open) No. 52-50352.

In the method for measuring endotoxin according to this invention, endotoxin may be measured according to a conventional endotoxin measuring method using the reagent thus prepared. Other reagents and the like used in the method of this invention may be properly chosen in accordance with reagents used in a conventional endotoxin measuring method. More in detail, endotoxin can be measured as follows.

(i) Gel-clot technique

This technique comprises mixing the reagent of the present invention with a sample, incubating the resulting mixture at a temperature of 0° to 40° C., preferably 25° to 40° C., for a predetermined time, and judging with the naked eye whether a gel is produced by coagulation or not.

(ii) End point-turbidimetric technique

This technique comprises mixing the reagent of the present invention with a sample, incubating the resulting mixture at a temperature of 0° to 40° C., preferably 25° to 40° C., for a predetermined time, and measuring a turbidity due to coagulation using a coagulometer, a nepherometer, a spectrophotometer, or the like.

(iii) Kinetic tubidimetric technique

This technique comprises mixing the reagent of the present invention with a sample, incubating the resulting mixture at a temperature of 0° to 40° C., preferably 25° to 40° C., for a predetermined time, and measuring a time required for a turbidity change due to coagulation to reach a designated value or a ratio in change of the turbidity using a coagulometer, a nepherometer, a spectrometer, or the like.

(iv) Chromagenic technique

This technique comprises mixing the reagent of the present invention with a sample and a synthetic substrate such as Boc-Val-Leu-Gly-Arg-p-nitroaniline, Boc-Val-Leu-Gly-Arg-[(4-N-ethyl-N-2-hydroxyethyl) aminoaniline, etc. of protease which is activated by the reaction of a component of the AL solution with endotoxin, incubating the resulting mixture at a temperature of 0° to 40° C., preferably 25° to 40° C., for a predetermined time, then if necessary adding a stopper for protease reaction, and measuring a substance released from the synthetic substrate by protease activity colorimetrically, or the like. The range of application of this invention is not limited to these methods, and this invention is applicable to any measuring method utilizing a reaction of AL with endotoxin.

In the measuring method of this invention, as the pH at the time of measurement, any pH may be employed so long as it does not inactivate the factors which reacts with endotoxin in AL solution to cause coagulation reaction, though a pH in the range of 6 to 8 is usually preferably employed. As the temperature at the time of measurement, any temperature may be employed so long as it does not inactivate the factors which reacts with endotoxin in AL solution to cause coagulation reaction, though a temperature of 0° to 40° C., preferably 25° to 40° C. is usually employed.

The reagent specific for ET obtained by the process of this invention can be stably stored by freezing or freeze-drying, and therefore when it is prepared in a large amount, it may be stored by these methods.

This invention is more concretely illustrated by way of the following Examples, but not limited thereto.

EXAMPLE 1

Preparation of a reagent by use of curdlan

To 1 g of curdlan (available from Wako Pure Chemical Industries, Ltd.) was added 100 ml of distilled water for injection, and the resulting mixture was filtered through a sterilized glass filter. The above procedure was repeated 5 times, and about 10 mg of the curdlan thus obtained was suspended in about 10 ml of distilled water for injection. The resulting suspension was filtered through a membrane filter having a pore size of 0.45 μm. A freeze-dried product of AL solution derived from horseshoe crab belonging to Limulus genus (hereinafter the freeze-dried product being abbreviated as "LAL"; available from ACC; gelation sensitivity 0.5 Eu/ml; for dissolution in 5 ml) was dissolved in 5 ml of distilled water for injection, and the resulting LAL solution was filtered through the filter having curdlan adhered to the surface, to obtain a desired reagent specific for ET (hereinafter abbreviated as "CT-LAL solution").

EXAMPLE 2

Preparation of a reagent by use of zymosan

To 1 g of zymosan (available from Sigma Chem. Co., Ltd.) was added 100 ml of distilled water for injection, and the resulting mixture was filtered through a sterilized glass filter. The above procedure was repeated 10 times, and about 10 mg of the zymosan thus obtained was suspended in a LAL solution obtained by dissolving LAL (available from ACC; gelation sensitivity 0.5 Eu/ml; for dissolution in 5 ml) in 5 ml of distilled eater for injection. The resulting suspension was filtered through a membrane filter having a pore size of 0.45 μm to obtain a desired reagent specific for ET (hereinafter abbreviated as "ZT-LAL solution").

REFERENTIAL EXAMPLE 1

Samples

The following curdlan solutions and ET solutions were used as samples.

Curdlan solutions

There were used solutions prepared by dissolving curdlan containing non-detectable amount of ET (available from Wako Pure Chemical Industries, Ltd.) in a 50 mM ET-free aqueous sodium hydroxide solution to a concentration of 5 mg/ml, and diluting the resulting solution properly with distilled water for injection.

ET solutions

There were used solutions prepared by dissolving *Escherichia coli* control standard endotoxin (a lipopolysaccharide derived from *E. coli* UKT-B strain, available from Wako Pure Chemical Industries, Ltd.; each vial contained the lipopolysaccharide in an amount corresponding to 500 ng of FDA reference standard endotoxin EC-2; for dissolution in 5 ml) in 5 ml of distilled water for injection, and diluting the resulting solution properly with distilled water for injection.

Measuring procedure

To 0.1 ml of the CT-LAL solution prepared in Example 1 was added 0.1 ml of each sample, and after sufficient mixing, a time required for reducing the transmittance by 5% (hereinafter abbreviated as "Tg") was measured at 37° C. by means of a Toxinometer ET-201 (mfd. by Wako Pure Chemical Industries, Ltd.).

Results

In FIG. 1, a calibration curve shown by —O— is obtained by plotting the logarithm of Tg value on the axis of ordinate corresponding to the logarithms of individual ET concentrations on the axis of abscissa. When the curdlan solutions were used as samples, the transmittance of the sample was not reduced by 5% in 80 minutes at any of the curdlan concentrations (data was not shown).

COMPARATIVE EXAMPLE 1

Measurement was carried out for the same samples as in Referential Example 1 by the same measuring procedure as in Referential Example 1, except that a LAL solution prepared by dissolving LAL of the same lot as in Example 1 in 5 ml of distilled water for injection (hereinafter abbreviated as "untreated LAL solution") was used in place of the CT-LAL solution used in Referential Example 1.

Results

In FIG. 1, a calibration curve shown by -●- is obtained by plotting the logarithm of Tg value on the axis of ordinate corresponding to the logarithms of individual ET concentrations on the axis of abscissa. In FIG. 2, a calibration curve shown by -●- is obtained by plotting the logarithm of Tg value on the axis of ordinate corresponding to the logarithms of individual curdlan concentrations on the axis of abscissa.

As is clear from FIG. 1, when the ET solutions were used as samples, a calibration curve having a good linearity could be obtained by using either the CT-LAL solution or untreated LAL solution as a reagent for measuring ET.

As is clear from FIG. 2, untreated LAL solution reacts also with the curdlan solutions to result in a calibration curve having a good linearity.

It can be seen that as is clear from the above results, a reagent specific for ET can be obtained by treating AL solution according to the process of this invention.

REFERENTIAL EXAMPLE 2

In Table 1 are shown the results of measurement carried out by the same measuring procedure as in Referential Example 1 by using the sample containing 1.5 Eu/ml of endotoxin prepared in Referential Example 1 (sample-1) and a mixture of equal amounts of the sample containing 20 ng/ml of curdlan and the sample containing 3.0 EU/ml of endotoxin which had been prepared in Referential Example 1 (sample-2).

COMPARATIVE EXAMPLE 2

In Table 1 are also shown the results of measurement carried out for the same samples as in Referential Example 2 by the same measuring procedure as in Referential Example 2, except that the same untreated LAL solution as used in Example 1 was used in place of the CT-LAL solution used in Referential Example 2.

TABLE 1

| Sample | Referential Example 2 Tg (min.) | Comparative Example 2 Tg (min.) |
| --- | --- | --- |
| Sample-1 | 21.0 | 22.0 |
| Sample-2 | 20.8 | 13.2 |

It can be seen that as is clear from the results shown in Table 1, when the CT-LAL solution is used as a reagent for measuring ET, a TG value substantially equal to that obtained for the ET solution is obtained for the sample containing both ET and curdlan, thereby indicating that the CT-LAL solution does not react with curdlan. It can also be seen that when measurement is carried out using the untreated LAL solution as a reagent for measuring ET, Tg is greatly reduced by the addition of curdlan to ET solution, indicating that the untreated LAL solution reacts with both ET and curdlan.

REFERENTIAL EXAMPLE 3

Samples

The same as in Referential Example 1.

Measuring reagent

A measuring reagent was prepared by adding 1 ml of 0.45M N,N-bis(2-hydroxyethyl)-2-aminoethanesulfonic acid buffer (pH 7.5) and 1 ml of a substrate solution [containing 1.02 mM Boc-Val-Leu-Gly-Arg-[(4-N-ethyl-N-2-hydroxyethyl)aminoaniline (mfd. by Wako Pure Chemical Industries, Ltd.), 2.25 mM diethylaniline, and 0.12M magnesium chloride] to 1 ml of the ZT-LAL solution obtained in Example 2.

Measuring procedure

To 0.2 ml of the measuring reagent was added 0.1 ml of each sample, followed by sufficient mixing. The mixture was incubated at 37° C. for 30 minutes. After the incubation, the reaction was stopped by adding 1 ml of a reaction stopper solution containing 0.17% of sodium metaperiodate and 0.25% of sodium lauryl sulfate (SDS), and then absorbance at 730 nm of the reaction solution was measured.

Results

Figure 4:
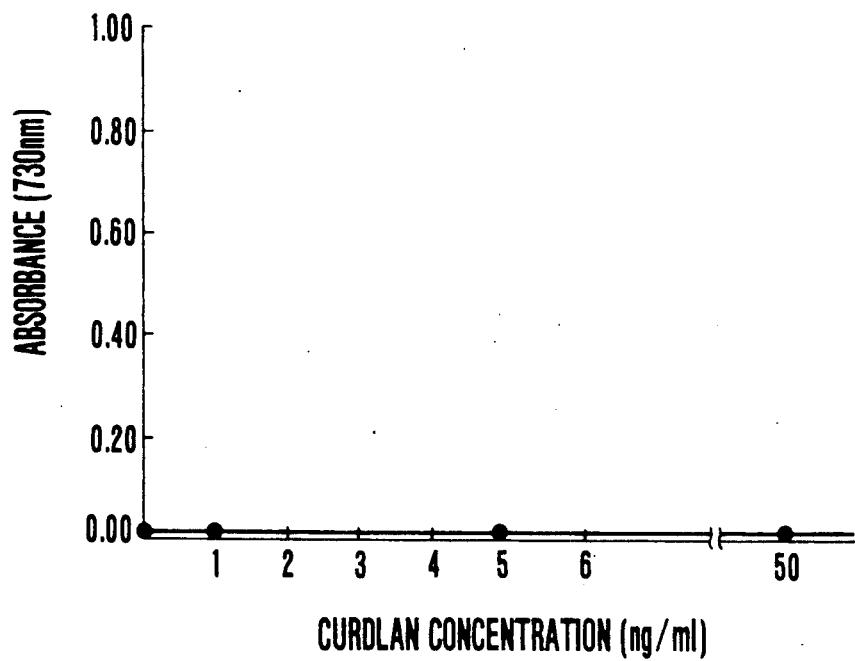
FIG. 4 shows a calibration curve for curdlan which was obtained in Referential Example 3.

In FIG. 3 is shown a calibration curve obtained by plotting absorbance on the axis of ordinate corresponding to individual ET concentrations on the axis of abscissa. In FIG. 4 is shown a calibration curve obtained by plotting absorbance on the axis of ordinate corresponding to individual curdlan concentrations on the axis of abscissa.

As is clear from FIG. 3 and FIG. 4, the ZT-LAL solution obtained by the process of this invention reacted with ET and showed a calibration relation having a good linearity, but it did not react with curdlan at any concentration.

When measurement was carried out using a mixture of equal amounts of the sample containing 20 ng/ml of curdlan and the sample containing 1.0 EU/ml of ET, absorbance at 730 nm of the reaction solution was 0.458, which was the same as that (0.450) measured for the sample containing 0.5 EU/ml of ET alone.

It can be seen that as is clear from these results, the ZT-LAL solution does not react with curdlan but is activated only by ET.

As described above, this invention provides a process which makes it possible to prepare a measuring reagent for measuring ET easily and efficiently by use of AL solution as a starting material without any special procedure such as fractionation and recombination of components in the AL solution. Thus, this invention contributes greatly to the art.

What is claimed is:

1. A process for preparing a reagent for measuring endotoxin which comprises contacting an extracted solution of horseshoe crab hemocyte lysate with at least one treating agent selected from the group consisting of (a) a water-insoluble polysaccharide containing $\beta$-1,3-glucosidic linkage, (b) a water-insoluble polysaccharide derivative containing $\beta$-1,3-glucosidic linkage, (c) a polysaccharide containing $\beta$-1,3-glucosidic linkage and being fixed on a water-insoluble carrier, and (d) a polysaccharide derivative containing $\beta$-1,3-glucosidic linkage and being fixed on a water-insoluble carrier.

2. A process according to claim 1, wherein the treating agent is (a) a water-insoluble polysaccharide containing $\beta$-1,3-glucosidic linkage.

3. A process according to claim 2, wherein the treating agent is curdlan or zymosan.

4. A reagent for measuring endotoxin obtained by contacting an extracted solution of horseshoe crab hemocyte lysate with at least one treating agent selected from the group consisting of (a) a water-insoluble polysaccharide containing $\beta$-1,3-glucosidic linkage, (b) a water-insoluble polysaccharide derivative containing $\beta$-1,3-glucosidic linkage, (c) a polysaccharide containing $\beta$-1,3-glucosidic linkage and being fixed on a water-insoluble carrier, and (d) a polysaccharide derivative containing $\beta$-1,3-glucosidic linkage and being fixed on a water-insoluble carrier.

5. A process for determining the presence of endotoxin in a sample, which comprises mixing the reagent of claim 4 with the sample, incubating the resulting mixture, and observing whether a gel is produced.

6. A process for measuring endotoxin, which comprises mixing the reagent of claim 4 with a sample, incubating the resulting mixture, and measuring turbidity due to coagulation.

7. A process for measuring endotoxin, which comprises mixing the reagent of claim 4 with a sample, incubating the resulting mixture and measuring the time required for turbidity due to coagulation to reach a predetermined value.

8. A process for measuring endotoxin, which comprises mixing the reagent of claim 4 with a sample together with a synthetic substrate of protease, incubating the resulting mixture, and measuring a substance released from the synthetic substrate by protease activity.

* * * * *